US00PP21463P2

(12) United States Plant Patent
Laviana

(10) Patent No.: US PP21,463 P2
(45) Date of Patent: Nov. 9, 2010

(54) ***CAREX* PLANT NAMED 'ICE CREAM'**
(50) Latin Name: *Carex oshimensis*
Varietal Denomination: Ice Cream

(75) Inventor: Marc R. Laviana, Kensington, CT (US)

(73) Assignee: Sunny Border Nurseries, Inc., Kensington, CT (US)

( * ) Notice: Subject to any disclaimer, the term of this patent is extended or adjusted under 35 U.S.C. 154(b) by 0 days.

(21) Appl. No.: 12/462,804

(22) Filed: Aug. 10, 2009

(51) Int. Cl.
*A01H 5/00* (2006.01)

(52) U.S. Cl. ..... Plt./384
(58) Field of Classification Search ..... Plt./384

See application file for complete search history.

*Primary Examiner*—Annette H Para
*Assistant Examiner*—Louanne C Krawczewicz Myers
(74) *Attorney, Agent, or Firm*—Penny J. Aguirre

(57) ABSTRACT

A new cultivar of *Carex oshimensis*, 'Ice Cream', characterized by its variegated foliage with wide, dark green margins and creamy white centers, its relatively vigorous growth habit and its hardiness at least in U.S.D.A. Zones 5 to 9.

1 Drawing Sheet

Botanical classification: *Carex oshimensis.*
Varietal denomination: 'Ice Cream'.

BACKGROUND OF THE INVENTION

The present invention relates to a new and distinct cultivar of *Carex oshimensis* and will be referred to hereafter by its cultivar name, 'Ice Cream'. 'Ice Cream' is a new cultivar of perennial ornamental grass grown for container and landscape use, primarily in shaded exposures.

The Inventor discovered 'Ice Cream' in summer of 2007 in a container in his nursery in Kensington, Conn. 'Ice Cream' arose as a naturally occurring chimeral mutation of *Carex oshimensis* 'Evergold' (not patented).

Asexual reproduction of the new cultivar was first accomplished by rhizome division in Kensington, Conn. in 2007 by the Inventor. The characteristics of this cultivar have been determined to be stable and are reproduced true to type in successive generations both by division and in vitro propagation.

SUMMARY OF THE INVENTION

The following traits have been repeatedly observed and represent the characteristics of the new cultivar. The new *Carex* has not been observed under all possible environmental conditions. These attributes in combination distinguish 'Ice Cream' from all other selections of *Carex* known to the Inventor.

1. 'Ice Cream' exhibits variegated foliage with wide, dark green margins and creamy white centers.
2. 'Ice Cream' exhibits a more vigorous growth habit in comparison to its parent plant.
3. 'Ice Cream' is hardy at least in U.S.D.A. Zones 5 to 9.

'Ice Cream' can be most closely compared to its parent, 'Evergold'. 'Evergold' differs from 'Ice Cream' in having narrower green margins and a slower growth habit. 'Ice Cream' can also be compared to the cultivar 'Gold Strike' (unpatented). 'Gold Strike' is also variegated with creamy white centers and green margins however 'Gold Strike' differs from 'Ice Cream' in having very fine green margins and a very dense compact habit.

BRIEF DESCRIPTION OF THE DRAWING

The accompanying colored photograph was taken of a one year-old plant of 'Ice Cream' as grown in a one-gallon container outdoors in Kensington, Conn. The photograph on FIG. 1 provides a view of the variegation, flowers, and plant habit of 'Ice Cream'. The colors of the new *Carex* in the photograph may differ slightly from the color values cited in the detailed botanical description, which accurately describe the colors of the new *Carex*.

DETAILED BOTANICAL DESCRIPTION

Figure 1:
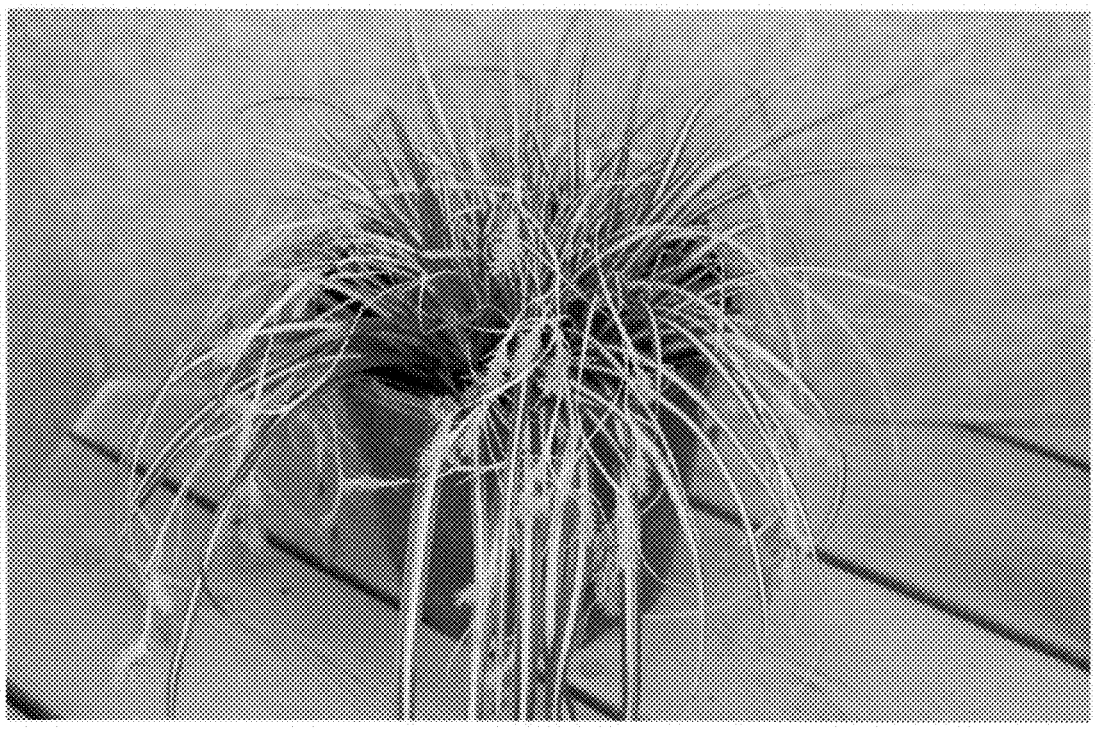

The general observations and descriptions describe plants of 'Ice Cream' as grown outdoors in a one-gallon in Kensington, Conn. for one year from a single rhizome division. The phenotype may vary somewhat with variations in temperature, day-length, light intensity, soil types, and water and fertility levels without, however, any variance in genotype. The color determinations are in accordance with The 2007 R.H.S. Colour Chart of The Royal Horticultural Society, London, England, except where general color terms of ordinary dictionary significance are used.

General description:

*Blooming period.*—Inflorescences emerge in spring and continue into summer in the Connecticut, the flowers are insignificant and 'Ice Cream' is grown for its foliage.

*Plant habit.*—Evergreen at least to U.S.D.A. Zone 5, clump-forming, mounded, arching and slowly spreading via rhizomes.

*Height and spread.*—Reaches about 20 cm in height and slowly spreads as a groundcover; a single division spreads to about 9 cm at the base and 36 cm to the edges of the foliage in one growing season.

*Hardiness.*—At least in U.S.D.A. Zones 5 to 9.

*Culture.*—Grows best in part shade in fertile, well-drained soils with adequate moisture, tolerant to full shade in warmer climates and full sun in cooler climates.

*Diseases and pests.*—*Carex oshimensis* is typically unaffected by disease and pests.

*Root description.*—Short, stout rhizomes with fibrous roots.

*Propagation.*—Rhizome division.

*Growth rate.*—Vigorous.

*Branching.*—Stemless, shoots arise from rhizomes.

Foliage description:

*Leaf shape.*—Linear.

*Leaf division.*—Simple.

*Leaf base.*—Sheathed to rhizome.

*Leaf apex.*—Attenuate.

*Leaf aspect.*—Leaves initially emerge upright, then cascade at an average of a 45° angle.

*Leaf venation.*—Parallel, the midrib is raised on the lower surface, not prominent or conspicuous, color matches leaf color.

*Leaf margins.*—Entire, scaberulose towards apex.

*Leaf persistence.*—Persistent; evergreen under conditions tested.

*Leaf attachment.*—Sheathed.

*Leaf size.*—Matures to an average of 26 cm in length and 8 mm in width.

*Leaf number.*—Average of 15 leaves per rhizome and about 250 per plant with a base width 9 cm.

*Leaf arrangement.*—Equitant (overlapping), emerge from center, sheathed to base.

*Leaf surface.*—Glabrous on upper and lower surface, semi-glossy on upper surface.

*Leaf variegation pattern.*—Creamy white centers and green margins with centers comprising one third to one half of the leaf area.

*Leaf color.*—Emerging leaf color upper surface; centers 157D with margins 144A, emerging leaf color lower surface: centers 157D with margins 138B, mature leaf color upper surface: centers 150D with margins 137B, mature leaf color lower surface; centers 150D with margins 138A.

Flower description:

*General description.*—Terminal racemes of pistillate spikelets.

*Inflorescence size.*—Averages 10 cm in height and 1.5 cm in width.

*Flower quantity per inflorescence.*—Typically 25 florets per spikelet, an average 4 spikelets per raceme.

*Lastingness of inflorescence on the plant.*—About 10 days.

*Fragrance.*—None.

*Floret buds.*—Narrowly ovate in shape, about 2 mm in length and about 1 mm in diameter, 138B in color.

*Spikelet aspect.*—Nearly upright.

*Spikelet shape.*—Sedge-like, narrowly obovate.

*Spikelet color.*—Emerge 144B with extended pistils 161C, dries to 165A with pistils 161A.

*Persistence of spikelets.*—Persistent.

*Floret size.*—An average of 2.5 mm in diameter and 9 mm in length.

*Floret description.*—1 glume on outer side and 2 lemma on inner side, glumes; an average of 8 mm in length and 0.8 mm in width, lanceolate in shape, margin entire, apex narrowly acute, color of upper and lower surface N144D, surface is smooth and dull in appearance, lemma; an average of 5 mm in length and 2 mm in width, narrowly ovate in shape, margin entire, apex long and mucronate, color of upper and lower surface 144B, surface is smooth and dull in appearance.

*Flower stem.*—An average of 19 cm in length (including rachis about 10 cm in length) and 3 mm in width, 150D in color, surface is glabrous, an average of 2 stem leaves per stem; an average of 5 cm in length and 2 mm in width, 145D in color with thin margin of 145B, surface is glabrous.

*Rachilla.*—An average of 1 cm in length and 1 mm in diameter, held upright, glabrous surface, 150D in color.

Reproductive organs:

*Gynoecium.*—Average of 3 pistils about 7 mm in length, stigma is fimbriate, about 2 mm in length and 161C in color, style is about 0.2 mm in length, insufficient in size to be color coded, ovary is oblong in shape, about 1.5 mm in length, and 145A in color.

*Androcoecium.*—No stamens observed.

*Fruits and seeds.*—Seed production has not been observed to date.

It is claimed:

1. A new and distinct cultivar of *Carex* plant named 'Ice Cream' as herein illustrated and described.

* * * * *